July 26, 1949. F. P. MERRITT Plant Pat. 856
CLIMBING ROSE PLANT
Filed June 26, 1947
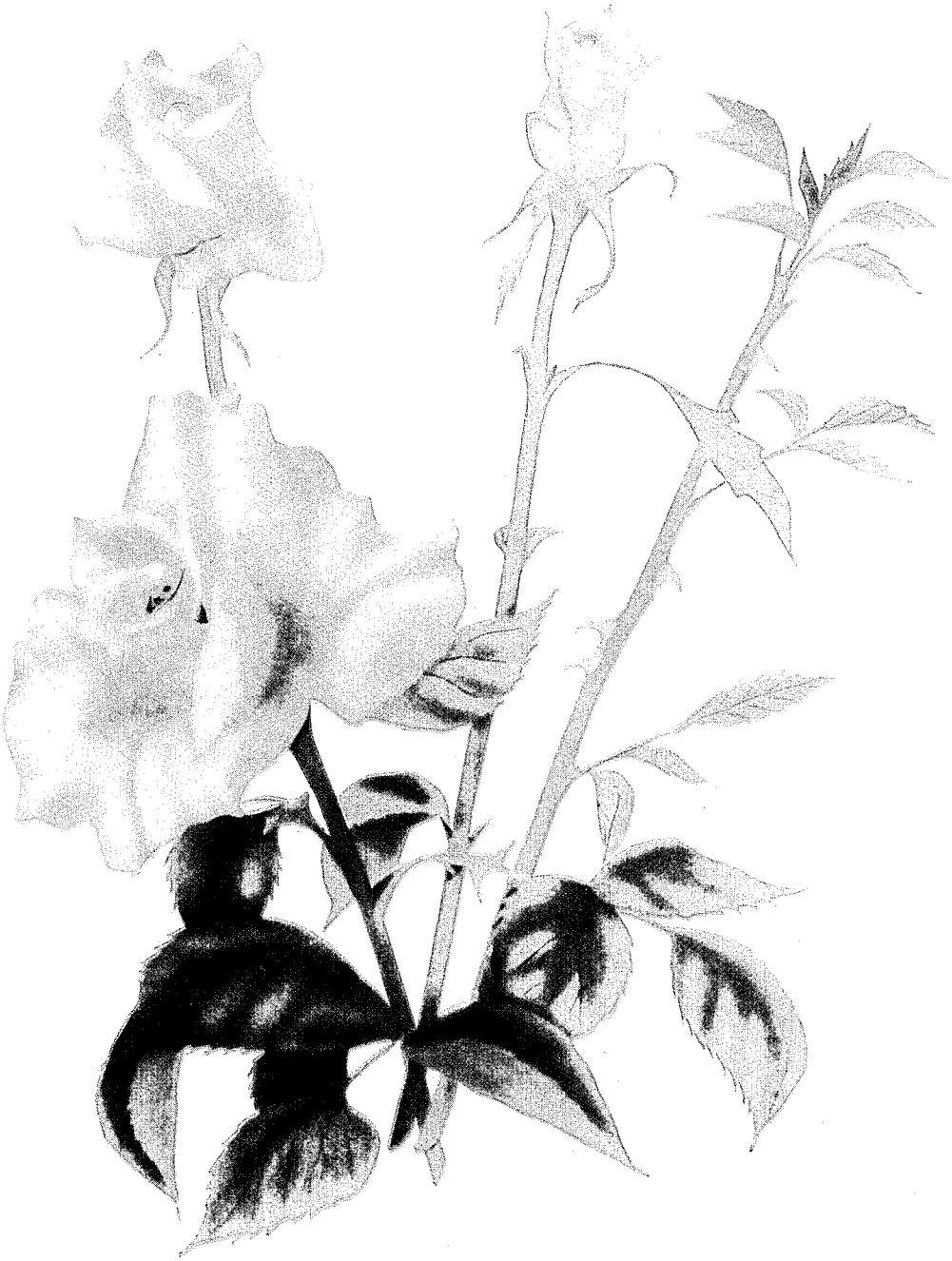
INVENTOR
Frank P Merritt
BY Orville M. Kile
Plant Pat. Agt.

Patented July 26, 1949

Plant Pat. 856

UNITED STATES PATENT OFFICE

856

CLIMBING ROSE PLANT

Frank P. Merritt, Hamilton, Mont.

Application June 26, 1947, Serial No. 757,171

1 Claim. (Cl. 47—61)

My present discovery relates to a new and distinct variety of climbing hybrid tea rose plant, which originated as a sport from the variety Hoosier Beauty and was discovered by me in my greenhouses.

This new variety is an exceptionally vigorous, everblooming climber with heavy stalk, producing large double flowers on stems unequalled for length by any other climbing rose and it combines a greater number of desirable qualities than are possessed by any other variety of rose known to me. It has been asexually reproduced and grown by me through several generations without evidencing any change of its original characteristics.

Accompanying illustrations show three specimens of the flowers of my new variety in various stages of opening, in approximately their true colors. It must be borne in mind, however, that with the medium of water colors it is difficult to show the satiny sheen of the petals.

Following is a more detailed description of the plant and flower of my new variety. Color names and references are in accordance with Ridgway's Color Standards and Nomenclature.

*The plant*

Growth habit: Very vigorous, strong climbing rose, attaining a height of 12 feet or more. Branches freely.

Blooming habit: Continuous and prolific.

Disease resistance: Particularly resistant to mildew and blackspot.

Stems:

*Size.*—Exceptionally long and strong. This variety has produced stems or canes up to 60 inches in length with a majority of the stems 24 to 36 inches long.

*Color.*—Light green to medium green, approximately Grass Green (Plate VI), with reddish tinge. New stems from Hazel (Plate XIV) to Jasper Red (Plate XIII).

*Surface.*—Very smooth with the exception of a few irregularly placed thorns principally on lower part of stem. Thorns are downward hooked and very red on new wood with reddish tinge on old wood.

*Nodes.*—Heavy; moderately close-set; staggered.

Foliage: Compound, with 3 to 7 leaflets.

*Quantity.*—Heavy and abundant.

*Shape.*—Oval, extended to a long sharp point at apex. Margins deeply and sharply serrated.

*Size.*—Large, averaging 2 inches wide by 3 inches long for terminal leaflet.

*Color.*—New growth very red on under surface and reddish on upper surface. Older growth approximately Grass Green (Plate VI), sometimes with reddish tinge.

*Aspect.* — Upper surface smooth, reverse rough. Ribs and veinings prominent.

*Rachis.*—Upper surface slightly grooved; few spines on under surface.

*Stipules.*—Long, narrow and smooth. Tightly clinging except for points which turn out abruptly.

Bud:

*Shape.*—Moderately long-pointed, later developing urn-shaped.

*Opening.*—Opens very slowly and revolutely. Outer petals curl and reflex as bud opens.

*Color.*—Not found in Ridgway's but most nearly approaches Tyrian Rose (Plate XII).

*Sepals.*—Medium in length, slightly foliaceous, and tinged with red. Reflex early as bud develops.

*Receptacle.*—Funnel-shaped; smooth, dark green.

*Peduncle.*—Moderate length, rigid, slightly flattened, green with reddish tinge.

Bloom:

*Form.*—Full high-centered form, which is retained. Stamens and pistils are disclosed only in advanced stages of development. Petals are arranged revolutely, evenly graduated in size.

*Size.*—Large, measuring about 5 inches in diameter when fully expanded.

*Petalage.*—Double, averaging 50 to 60 petals throughout the year when grown under glass.

*Color.*—General color effect might be called bright fiery crimson. This color is not found in Ridgway's but it approaches Tyrian Rose (Plate XII), with darker veinings and shadings. The base of the petal has a small area of Chalcedony Yellow (Plate XVII) on its inner surface.

*Longevity.*—Flowers remain fresh for several days after full development on the plant, and also last unusually well as cut flowers.

*Fragrance.* — Very pronounced, lasting throughout the life of the flower.

Petals:

*Shape.*—Nearly round, with sharp point at apex and edge rather ruffled.

*Size.*—Large.

*Texture.*—Heavy and substantial.

*Aspect.*—Brilliant satiny sheen on inner surface.

*Behavior.*—Drop few at a time until all have fallen when flower dies.

*Comparison*

The principal points of difference between my new variety and its parent, Hoosier Beauty, are as follows:

1. My new variety is of a different color.
2. My new variety is a more vigorous and rapid growing plant.

3. The flowering of my variety is more free and more continuous.
4. The flowers of my variety are fuller and more perfectly formed.
5. The flowers of my variety are produced on far longer and stronger stems.
6. The flowers of my variety have more prolonged fragrance.
7. My new variety is a vigorous climber, while its parent is a bush rose.

Having thus disclosed my discovery, I claim:

The new and distinct variety of climbing hybrid tea rose plant substantially as herein disclosed, and characterized particularly by its extreme vigor; strong constitution; resistance to disease; long heavy stalks and stems; and prolific and continuous production of highest quality flowers of large size, perfect form, substantial texture, pronounced and prolonged fragrance, excellent keeping qualities, and distinctive coloring approximating Tyrian Rose.

FRANK P. MERRITT.

No references cited.